United States Patent

Kwetkat et al.

[11] Patent Number: 5,997,610
[45] Date of Patent: Dec. 7, 1999

[54] AMPHIPHILIC COMPOUNDS WITH AT LEAST TWO HYDROPHILIC AND AT LEAST TWO HYDROPHOBIC GROUPS BASED ON DICARBOXYLIC ACID DIAMIDES

[75] Inventors: Klaus Kwetkat, Lünen; Wulf Ruback, Dülmen, both of Germany

[73] Assignee: Huels Aktiengesellschaft, Marl, Germany

[21] Appl. No.: 08/894,221

[22] PCT Filed: Nov. 17, 1995

[86] PCT No.: PCT/EP95/04531

§ 371 Date: Aug. 18, 1997

§ 102(e) Date: Aug. 18, 1997

[87] PCT Pub. No.: WO96/25393

PCT Pub. Date: Aug. 22, 1996

[30] Foreign Application Priority Data

Feb. 17, 1995 [DE] Germany ............... 195 03 367

[51] Int. Cl.⁶ ................................................. C22B 1/00
[52] U.S. Cl. ................. 75/746; 510/119; 510/130; 510/276; 510/437; 554/44; 554/46; 554/47; 554/48; 554/50; 554/61; 554/63; 554/88; 554/110; 554/213; 560/127; 560/149; 560/150; 560/151; 560/174; 560/176; 560/186; 564/193; 564/197; 564/199; 424/70.1
[58] Field of Search .................. 554/96, 44, 46, 554/47, 48, 50, 61, 63, 69, 88, 102, 55, 103, 85, 108, 110, 213; 424/70.1; 510/130, 276, 119, 216, 437; 860/121, 149, 180, 181, 174, 176, 186; 564/193, 197, 194; 75/746

[56] References Cited

U.S. PATENT DOCUMENTS 5,160,450 11/1992 Okahara et al. .

FOREIGN PATENT DOCUMENTS 39 32 492  5/1991  Germany .
1-304 044  of 1989  Japan .

OTHER PUBLICATIONS

Abstract od JP–07003287, Jan. 1995.

Patent Abstracts of Japan, vol. 16, No. 383 (C–0974), Aug. 17, 1992, JP 4–124165, Apr. 24, 1994.

R. Zana, et al., Nature, vol. 362, pp. 228–230, Mar. 18, 1993, "Dependence of Aggregate Morphology on Structure of Dimeric Surfactants".

R. Zana, et al., Langmuir, vol. 7, No. 6, pp. 1072–1075, 1991, "Alkanediylα,ω–Bis(Dimethylalkylammonium Bromide) Surfactants. 1. Effect of the Spacer Chain Length on the Critical Micelle Concentration and Micelle Ionization Degree".

E. Alami, et al., Langmuir, vol. 9, No. 6, pp. 1465–1467, 1993, "Alkanediyl–α,ω–Bis(Dimethylalkylammonium Bromide) Surfactants. 3. Behavior at the Air–Water Interface".

*Primary Examiner*—Deborah D Carr
*Attorney, Agent, or Firm*—Oblon, Spivak, McClelland, Maier & Neustadt, P.C.

[57] ABSTRACT

The invention concerns amphiphilic compounds of general formula (I)

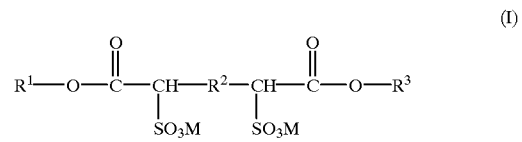

with at least two hydrophilic and at least two hydrophobic groups based on diacarboxylic acid diamides. The amphiphilic compounds according to the invention are mostly surface-active and are suitable for use as emulsifiers, demulsifiers, detergents, dispergents and hydrotropic agents in industry and households, for example, in the treatment of metals, ore processing, surface finishing, washing, cleaning, cosmetics, medicine and food processing and preparation.

7 Claims, No Drawings

AMPHIPHILIC COMPOUNDS WITH AT LEAST TWO HYDROPHILIC AND AT LEAST TWO HYDROPHOBIC GROUPS BASED ON DICARBOXYLIC ACID DIAMIDES

This application is a 371 of PCT/EP95/04531 filed Nov. 17, 1995.

BACKGROUND OF THE INVENTION

1. Field of the Invention

The invention relates to amphiphilic compounds with at least two hydrophilic and at least two hydrophobic groups based on dicarboxylic diesters.

2. Description of the Background

A wide variety of anionic, cationic, nonionic and zwitterionic compounds are known as amphiphilic substances. By far the most of these substances consist of a hydrophilic head group and at least one hydrophobic part.

With the amphiphilic substances there is a need, for ecological reasons, for example concerning the reduction in the cost of packaging and transport, to achieve an increasingly greater effect per mass of substance employed. Since optimization by mixing amphiphilic substances produces only very limited advances, novel amphiphilic substances with greater efficiency are required. It is therefore necessary in particular to find substances with lower critical micelle concentrations and/or lower surface and interfacial tensions in order to be able to reduce markedly the amounts of active substance used.

Initial approaches to a solution in this direction by doubling one part of the structure (hydrophilic head group, hydrophobic group) have already been disclosed. Thus, cationic surface-active compounds can be obtained by adding long-chain alkyl halides onto permethylated alkylenediamines [R. Zana, M. Benrraou, R. Rueff, Langmuir, 7 (1991) 1072: R. Zana, Y. Talmon, Nature, 362 (1993) 228; E. Alami, G. Beinert, P. Marie, R. Zana, Langmuir, 9 (1993) 1465].

Anionic surface-active compounds with at least two hydrophilic and at least two hydrophobic groups have to date been prepared only on the basis of diglycidyl ethers (U.S. Pat. No. 5,160,450, JP 01 304 033, JP 4 124 165). However, diglycidyl ethers are regarded as toxicologically objectionable and are rather costly. Furthermore, epichlorohydrin is used for their preparation, which leads to large amounts of residues so that these compounds are no longer in accord with the times from the ecotoxicological and economic viewpoints.

SUMMARY OF THE INVENTION

The object therefore was to find amphiphilic compounds which have at least two hydrophilic and at least two hydrophobic groups, the amphiphilic compounds having a very high efficiency relative to the amount used, and which furthermore can be prepared from raw materials which are easily available industrially and without large amounts of unwanted by-products being formed.

The object is achieved according to the invention by sulfonated, amphiphilic dicarboxylic diesters which can be prepared, for example, by sulfonation of dicarboxylic difatty alcohol esters or by sulfonation of dicarboxylic dialkyl esters with short alkyl chains and subsequent transesterification with fatty alcohols and neutralization of the sulfonic acids.

DETAILED DESCRIPTION OF THE INVENTION

The amphiphilic compounds according to the invention are compounds of the general formula I

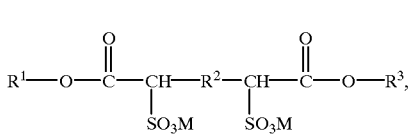

in which $R^1$, $R^2$ and $R^3$ in formula I have the meanings described below:

$R^1$ and $R^3$ are, independently of one another, an unbranched or branched, saturated or unsaturated hydrocarbon radical with 1 to 22, preferably 8 to 18, carbon atoms.

Specific substituents $R^1$ and $R^3$ which may be mentioned are the radicals methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-uneicosyl, n-docosyl and their branched-chain isomers, and the corresponding singly, doubly or triply unsaturated radicals.

$R^2$ is a spacer consisting of an unbranched or branched chain with 2 to 100 carbon atoms, which contains 0 to 20 oxygen and/or 0 to 20 nitrogen and/or 0 to 4 sulfur and/or 0 to 3 phosphorus atoms, and which has 0 to 20 functional side groups such as, for example, hydroxyl, carbonyl, carboxyl, amino and/or acylamino groups, and/or 0 to 4 rings, which are isolated or fused.

The spacer $R^2$ is, in particular, unbranched or branched alkylene chains of the formula II as basic skeleton

with a=2 to 18, preferably a=2 to 6;

unbranched or branched alkynylene chains of the formula III as basic skeleton

with d+e=2 to 16, where d and e are each greater than zero, and where in the compounds according to formulae II and III the spacer may contain at any desired point in the chain additionally 1 to 4 carbonyl, carboxyl, amino or acylamino groups;

alicycles according to the formula IV

with f and g each equal, independently of one another, to 1 to 6 or according to formula V

-3(4), 8(9)-di(methylene)-tricyclo[5.2.1.0$^{2.6}$]decane- (V);

unsubstituted or substituted aromatics according to the formula VI

or according to the formula VII

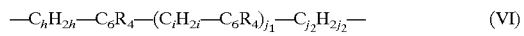

with h, j, $j_1$ and $j_2$ each equal, independently of one another, to 0 to 8 and i=1 to 8 and with R equal, independently of one another in each case, to H or $C_1$- to $C_6$-alkyl;

a chain with 0 to 20 functional side groups, where the functional side groups are hydroxyl, carbonyl, carboxyl, amino and/or acylamino groups, and/or 0 to 4 rings, which are isolated or fused.

Furthermore, the spacer $R^2$ contains in each case 0 to 20, preferably 1 to 12, oxygen and/or nitrogen atoms, and/or 0 to 4 sulfur atoms and/or 0 to 3 phosphorus atoms.

$R^2$ thus furthermore has in particular the meaning of a compound according to the formula VIII

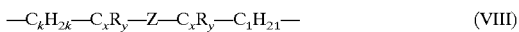

with k and l each equal, independently of one another, to 0 to 8, x=6 and y=4 or x=10 and y=6 or x=14 and y=8, and Z=O, CO, NH, N—$CH_2$—CH(OX)—$R^1$, $NR^1$, N—C(O)$R^1$, $SO_2$ or according to the formula IX

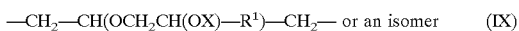

with X=$SO_3$M or 2,2'-methylenebis(1,3-dioxolane-5-methylene)—or acetals, especially diacetals of dialdehydes and di-, oligo- or polyols, where $R^1$ denotes a hydrocarbon radical with 1 to 22 carbon atoms, of a compound according to the formula X

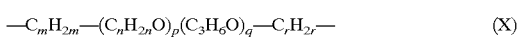

with m=1 to 4, n=2 to 4, p=1 to 20, preferably p=1 to 4, q=0 to 4 and r=1 to 4, where mixed alkoxide units may also occur and then the sequence of the alkoxide units is arbitary;

of a compound according to the formula XI

or according to the formula XII

or according to the formula XIII

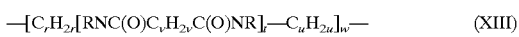

or according to the formula XIV

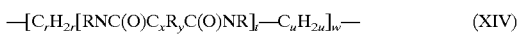

with r=2 to 4, s=2 to 4, t=1 to 20, preferably t=1 to 4, u=2 to 4, v=0 to 12, w=1 to 6, x=6 and y=4 or x=10 and y=6 or x=14 and y=8 with R equal, independently of one another, to H or $C_1$- to $C_6$-alkyl, with M, M'=alkali metal, ammonium, alkanolammonium or ½ alkaline earth metal.

German Offenlegungsschrift DE 39 32 492 describes salts of sulfonated esters of unsaturated dicarboxylic acids with unsaturated fatty alcohols. However, the structures of these compounds are entirely different from those of the compounds according to the invention because in DE 39 32 492 $SO_3$ is added exclusively onto double bonds.

The amphiphilic compounds according to the invention are usually distinguished by extremely low critical micelle concentrations (CMC) and very low surface and interfacial tensions (for example in the presence of paraffin), which must be ascribed to their special structure—at least two hydrophilic groups and at least two hydrophobic groups. Furthermore, most of them display a rather high hydrophilic suspension capacity which is about halfway between that of conventional surfactants and that of pentasodium tripolyphosphate. Some of these compounds are extremely rapid wetting agents.

The amphiphilic compounds according to this invention are particularly suitable as emulsifiers, demulsifiers, detergents, dispersants and hydrotropes in industry and domestically, for example in the areas of metal processing, ore production, surface treatment, washing and cleaning, cosmetics, medicine and foodstuff processing and preparation.

In these cases they can be combined with all customary anionic, nonionic, cationic and ampholytic surface-active substances. Examples of nonionic surface-active substances which can be used for a combination and which may be mentioned are: fatty acid glycerides, fatty acid polyglycerides, fatty acid esters, ethoxylates of higher alcohols, polyoxyethylene fatty acid glycerides, polyoxyethylene/propylene glycol fatty acid esters, polyoxyethylene sorbitan fatty acid esters, polyoxyethylene castor oil or hardened castor oil derivatives, polyoxyethylene lanolin derivatives, polyoxyethylene fatty acid amides, polyoxyethylene alkylamines, alkanolamines, alkylamine oxides, derivatives of protein hydrolysates, hydroxy-mixed ethers, alkyl polyglycosides and alkylglucamides.

Examples of anionic surface-active substances which can be used for combinations and which may be mentioned are: soaps, ether carboxylic acids and salts thereof, alkylsulfonates, α-olefinsulfonates, sulfonates of higher fatty acid esters, alcohol sulfates, alcohol ether sulfates, hydroxy-mixed ether sulfates, salts of phosphate esters, taurides, isethionates, linear alkylbenzenesulfonates, cumenesulfonate, alkylarylsulfonates, sulfates of polyoxyethylene fatty acid amides and salts of acylamino acids.

Examples of customary cationic surface-active substances which can be used for combinations and which may be mentioned are: alkyltrimethylammonium salts, dialkyldimethylammonium salts, alkyldimethylbenzylammonium salts, alkylpyridinium salts, alkylisoquinolinium salts, benzethonium chlorides and cationic acylamino acid derivatives.

Examples of ampholytic surface-active substances which can be used for combinations and which may be mentioned are: amino acids, betaines, sulfobetaines, imidazoline derivatives, soya oil lipids and lecithin.

Furthermore, the amphiphilic compounds according to the invention can also be combined together on their own.

It is likewise possible to add conventional additives to the amphiphilic compounds according to the invention. Such additives are specifically selected for a formulation and normally comprise inorganic salts such as sodium chloride and sulfate, and builders, hydrotropes, UV absorbers, softening agents, chelating agents, viscosity modifiers and fragrances.

The abovementioned compounds can be prepared, for example, by double sulfonation of the dicarboxylic difatty alcohol esters or by double sulfonation of dicarboxylic dialkyl esters with short alkyl chains and subsequent transesterification with fatty alcohols and neutralization of the sulfonic acids with aqueous alkali metal or alkaline earth metal hydroxides or ammonia or alkanolamines. If required, the products are bleached in aqueous solution with hydrogen peroxide (0.1 to 2.0% based on solid).

We claim:

1. An amphiphilic compound of formula (I):

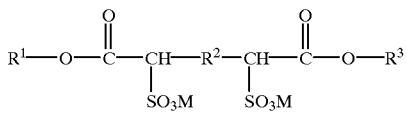

wherein $R^1$ and $R^3$ denote, independently of one another, a saturated or unsaturated, unbranched or branched hydrocarbon radical having 1–22 carbon atoms; M and M' each denote alkali metal, ammonium, alkanolammonium or ½ alkaline earth metal and $R^2$ denotes a spacer selected from the group consisting of:

(i) an unbranched or branched alkylene chain of formula (II):

     (II)

wherein a is an integer ranging from 2–18;

(ii) an alicyclic group of formula (IV):

     (IV)

wherein f and g each equal, independently of one another, to 1–6;

(iii) a group of formula (V):

-3(4),8(9)-di(methylene)-tricyclo-[5.2.1.0$^{2.6}$]decane-   (V);

(iv) an unsubstituted or substituted aromatic group of formula VI:

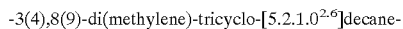     (VI)

or a group (v) of formula (VII):

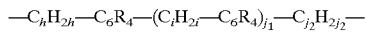     (VII)

wherein h, j, $j_1$ and $j_2$ each equal, independently of one another, 0–8 and i=1–8 and with each R equal, independently of one another, to H or $C_1$- to $C_6$-alkyl;

(vi) a group formula (VIII):

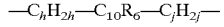     (VIII)

with k and 1 each equal, independently of one another, to 0–8; x=6 and y=4 or x=10 and y=6 or x=14 and y=8; each R is hydrogen or $C_1$–$C_6$-alkyl and Z=O, CO, NH, $NR^1$, $N—CH_2—CH(OX)—R^1$, $N—C(O)R^1$ or $SO_2$;

(vii) a group of formula (IX):

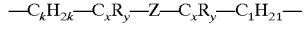     (IX)

wherein $X=SO_3M$ and $R^1$ is a hydrocarbon radical of 1–22 carbon atoms;

(viii) a group of formula (X):

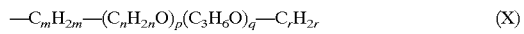     (X)

wherein m=1–4, n=2–4, p=1–20, q=0–4 and r=1–4, and wherein, optionally, mixed alkoxide units, in any arbitrary sequence, are present in the group;

(ix) -2,2'-methylene-bis(1,3-dioxolane-5-methylene)-;

(x) $R^2$ denotes acetal;

(xi) a group of formula (XI):

     (XI);

(xii) a group of formula (XII):

     (XII);

(xiii) a group of formula (XIII):

     (XIII);

or (xiv) a group of formula (XIV):

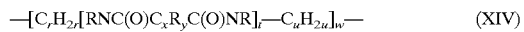     (XIV)

wherein, in formulas (XI)–(XIV), where appropriate, r=2–4, s=2–4, t=1–20, u=2–4, v=0–12, w=1–6, and x=6 and y=4 or x=10 and y=6 or x=14 and y=8, and wherein each R equals, independently of one another, H or $C_1$–$C_4$-alkyl.

2. A method of emulsifying or demulsifying a substance, comprising:

emulsifying or demulsifying said substance in a fluid medium containing the amphiphilic compound of claim 1.

3. A method of treating a metal, comprising:

contacting the metal with a fluid medium containing the amphiphilic compound of claim 1.

4. A method of treating an ore, comprising:

contacting the ore with an fluid medium containing the amphiphilic compound of claim 1.

5. A method of treating a surface, comprising:

contacting the surface with a fluid medium containing the amphiphilic compound of claim 1.

6. A method of washing or cleaning, comprising:

contacting a textile with a fluid medium containing the amphiphilic compound of claim 1.

7. A method of cleaning or washing the skin and/or hair, comprising:

contacting the skin and/or hair with a fluid medium containing the amphiphilic compound of claim 1.

* * * * *